US006317633B1

(12) United States Patent
Jorgenson et al.

(10) Patent No.: US 6,317,633 B1
(45) Date of Patent: Nov. 13, 2001

(54) IMPLANTABLE LEAD FUNCTIONAL STATUS MONITOR AND METHOD (75) Inventors: David J. Jorgenson, Bloomington; Ross O. Starkson, Minneapolis; Rick D. McVenes, Isanti; Charles D. Trautmann, Ham Lake; John D. Wahlstrand, Shoreview; Bradley C. Peck, Ham Lake, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/487,562

(22) Filed: Jan. 19, 2000

Related U.S. Application Data
(60) Provisional application No. 60/116,320, filed on Jan. 19, 1999.

(51) Int. Cl.[7] .................................................. A61N 1/37
(52) U.S. Cl. ........................................................ 607/28
(58) Field of Search ................................ 607/8, 28, 122

(56) References Cited

U.S. PATENT DOCUMENTS

| 4,140,131 | 2/1979 | Dutcher et al. | 128/419 PT |
|---|---|---|---|
| 4,549,548 | 10/1985 | Wittkampf et al. | 128/419 PG |
| 4,606,349 | 8/1986 | Livingston et al. | 128/419 PG |
| 4,825,869 | 5/1989 | Sasmor et al. | 128/419 PT |
| 4,899,750 | 2/1990 | Ekwall | 128/419 PG |
| 5,003,975 | 4/1991 | Hafelfinger et al. | 128/419 PG |
| 5,137,021 | 8/1992 | Wayne et al. | 128/419 PT |
| 5,156,149 | 10/1992 | Hudrlik | 128/419 PG |
| 5,184,614 | 2/1993 | Collins | 128/419 PG |
| 5,201,808 | 4/1993 | Steinhaus et al. | 128/419 PG |
| 5,201,865 | 4/1993 | Kuehn | 128/419 PT |
| 5,224,475 | 7/1993 | Berg et al. | 128/419 D |
| 5,282,840 | 2/1994 | Hudrlik | 607/28 |
| 5,344,430 | 9/1994 | Berg et al. | 607/8 |
| 5,350,410 | 9/1994 | Kieks et al. | 607/28 |
| 5,431,692 | 7/1995 | Hansen et al. | 607/28 |
| 5,453,698 | 9/1995 | Williams et al. | 324/678 |

(List continued on next page.)

Primary Examiner—William Kamm
(74) Attorney, Agent, or Firm—Girma Wolde-Michael; Reed A. Duthler (57) ABSTRACT An implantable medical device (IMD) coupled with leads extending to body tissue providing storage of lead related data, monitoring of lead functional status, and indication of lead integrity to the clinician. A lead status monitor (LSM) processes lead related data in a system self test mode and provides a lead status report that identifies and declares conductor/connector issues, insulation issues, and electrode/tissue interface issues indicative of suspected lead related condition mechanisms for each lead employed in the IMD. The LSM operates employing a set of LSM rules that process measured lead impedance values and loss of capture (LOC) values. In a pacing system, particular LSM rules are defined that process periodically determined, pacing pulse characteristic at LOC and bipolar and unipolar lead impedance values that are measured periodically. The lead impedance values are compared to upper and lower limits or trip points of a normal impedance range. Simultaneously, significant changes in lead impedance are detected, and the unipolar impedance value is compared to the bipolar lead impedance value of each lead. Counts of deviations in lead impedances satisfying each LSM rule are maintained. Certain of the lead related condition mechanisms are declared if a count of lead impedance deviations meets a programmed threshold number of such lead impedance deviations within a further programmed number of sequential impedance measurements. Preferably, the pacing pulse strength or voltage at LOC (characterized as LOC_RHEOBASE herein) is periodically determined and compared to a reference LOC_RHEOBASE.

22 Claims, 5 Drawing Sheets

U.S. PATENT DOCUMENTS

| | | |
|---|---|---|
| 5,507,786 | 4/1996 | Morgan et al. ............... 607/27 |
| 5,534,018 | 7/1996 | Walhstrand ............... 607/27 |
| 5,549,646 | 8/1996 | Katz et al. ............... 607/8 |
| 5,660,183 | 8/1997 | Chiang et al. ............... 128/695 R |
| 5,722,997 | 3/1998 | Nedungadi et al. ............... 607/28 |
| 5,741,311 | 4/1998 | Mc Venes et al. ............... 607/28 |
| 5,755,742 | 5/1998 | Schuelke et al. ............... 607/27 |
| 5,814,088 | 9/1998 | Paul et al. ............... 607/28 |
| 5,861,012 | 1/1999 | Stroebel ............... 607/28 |
| 5,891,179 | 4/1999 | Er et al. ............... 607/27 |
| 5,897,577 | 4/1999 | Cinbis et al. ............... 607/28 |
| 5,899,925 | 5/1999 | Ochs et al. ............... 607/5 |
| 5,910,156 | 6/1999 | Cinbis et al. ............... 607/27 |

IMPLANTABLE LEAD FUNCTIONAL STATUS MONITOR AND METHOD

This patent application claims the benefit of U.S. Provisional Application No. 60/116,320 filed Jan. 19, 1999.

FIELD OF THE INVENTION

This invention relates to the field of implantable medical devices coupled with leads extending to body tissue and to the storage of lead related data, monitoring of lead functional status, and indication of lead integrity to the clinician.

BACKGROUND OF THE INVENTION

A wide variety of implantable medical devices (IMDs) for delivering a therapy or monitoring a physiologic condition which may employ one or more elongated electrical leads and/or sensors have been clinically implanted or proposed for clinical implantation in patients. A wide variety of electrical stimulation therapy delivery IMDs comprising hermetically sealed, implantable pulse generators (IPGs) and associated electrical leads are implanted in patients' bodies for delivering electrical energy to locations of the body. Such IMDs comprise cardiac pacemakers, implantable cardioverter/defibrillators (ICDs) and muscle, nerve, brain, and organ stimulators, etc.

The leads of such IMDs typically comprise a lead body extending between a proximal lead end and a distal lead end and incorporates one or more exposed electrode or sensor element located at or near the distal lead end. One or more elongated electrical conductor extends through the lead body from a lead connector element formed at a proximal lead end for connection with connector elements of the IPG or monitor and a sensor terminal or electrode located at the distal lead end or along a section of the lead body. Each electrical conductor is typically electrically isolated from any other electrical conductors and is encased within an outer sheath that electrically insulates the lead conductor from body tissue and fluids and prevents physical contact of the conductors with such body tissue and fluids.

Such leads may extend from a subcutaneous implantation site of the IPG or monitor module through a wide variety of pathways into or adjacent to various chambers of the heart, deeply into the brain, into a location within the spine, and into or adjacent other body organs, muscles and nerves. The leads must be formed with small diameter, highly flexible, reliable lead bodies that withstand degradation by body fluids and body movements that apply stress and strain to the lead body and the connections made to electrodes or sensor terminals. As lead bodies are made smaller and smaller and the number of lead conductors is increased or maintained, problems with lead insulation and integrity of lead conductors may become more prevalent. During implantation, lead body insulation can be inadvertently breached or coiled lead conductors can be crushed in minute areas and can be overlooked. Later, these defects may be magnified by exposure to body fluids and result in conductor related condition that is intermittent or which slowly or suddenly manifests itself.

For example, modern implantable cardiac pacemakers and ICDs comprise an IPG implanted subcutaneously remote from the heart and a pacing lead or leads extending from the IPG to a pace/sense electrode or electrodes located with respect to a particular heart chamber to deliver the pacing pulses and sense the cardiac P-wave or R-wave. The lead bodies of such cardiac leads are continuously flexed by the beating of the heart, and other stresses are applied to the lead body in part affected by the implantation route taken between the IPG and the heart chamber or cardiac vessel where the electrodes or sensors are located. Movements by the patient can also cause the route traversed by the lead body to be constricted, whereby shear forces are applied to the lead body sheath and electrical conductors. At times, the lead bodies can be slightly damaged during surgical implantation, and the slight damage may progress in the body environment until a lead conductor fractures and/or the insulation is breached. In most such cases, the effects of lead body damage progress from an intermittent manifestation to a more continuous lead related condition state with lead aging. In extreme cases, insulation of one or more of the electrical conductors may be breached, causing the conductors to contact one another or body fluids resulting in a low impedance or short circuit. Or a lead conductor may fracture and exhibit an intermittent or continuous open circuit resulting in an intermittent or continuous high impedance.

Other problems can arise at the proximal lead end where the electrical connection between the IPG or monitor connector elements and the lead connector elements may be intermittently or continuously disrupted, resulting in a high impedance or open circuit. Usually, such connector open circuit problems result from insufficient tightening of the connection at the time of implantation followed by a gradual loosening of the connection until contact becomes intermittent or open.

In addition, the lead distal end may become dislodged from connection or contact with cardiac tissue, resulting in intermittent or continuous loss of contact of a distal pace/sense electrode with the heart tissue. The dislodgement may leave the electrodes floating in the blood of a heart chamber. Or, "lead penetration" may occur during implantation or chronically wherein the distal end of the lead may be advanced too far into the heart tissue or advances partly through the myocardium. Alternatively, "exit block" may occur, wherein a foreign body reaction, e.g. tissue growth over the pace/sense electrode surface or inflammation of the cardiac tissue adjacent the pace/sense electrode surface increases the pacing or sensing threshold to a level that can result in loss of pacing or sensing.

When these lead problems manifest themselves, they can be collectively referred to for simplicity as a "lead related condition" event though the lead itself is intact. Such lead related conditions may also include a connector open circuit condition or lead dislodgement. It is necessary for the clinician to diagnose the nature of the lead related condition from the available data, test routines that are undertaken, and IMD and patient symptoms. Then, it is necessary for the clinician to take corrective action, e.g., to either replace the lead, reposition the electrodes or sensors or tighten the proximal connection. In severe cases, the lead related condition may result in depletion of the battery energy of the IMD, requiring its replacement.

Certain IPGs and monitors have been clinically used or proposed that also rely on lead borne physiologic sensors that monitor physiologic conditions, e.g., blood pressure, temperature, pH, blood gases, etc. Cardiac pacemakers employing such sensors use the processed sensor signals to regulate pacing characteristics, e.g., pacing rate and/or energy. Open circuit or short circuit lead conductor related conditions or connector or dislodgement related conditions can disable such sensors and compromise monitoring and/or pacing operations dependent upon true sensor output signals.

The ability to sense P-waves or R-waves accurately through a lead can be impaired by any of these lead related conditions. Complete lead breakage impedes any sensing functions, lead conductor fractures or intermittent contact can cause electrical noise that interferes with accurate sensing, and loss of contact of the pace/sense electrodes with responsive cardiac tissue can cause true cardiac signals to be distorted or attenuated.

In the context of cardiac pacing, a delivered pacing pulse "captures" the heart if its delivery through an active, cathodal, pace/sense electrode to the adjacent heart tissue causes or "evokes" a myocardial contraction and depolarization wave that is conducted through the myocardium away from that pace/sense electrode site. The increased impedance of the pacing path or the short circuit of lead conductors due to one of the above-described lead related conditions can reduce the effective pacing pulse energy below that sufficient to capture the heart, resulting in loss of capture (LOC). Commonly assigned U.S. Pat. No. 5,861,012 (Stroebel), incorporated herein by reference, describes several approaches to the determination of the pacing threshold energy that achieves capture and the adjustment of the pacing pulse peak voltage and pulse width to deliver adequate pacing energy to assure capture while avoiding delivery of excess energy that is wasteful of battery energy. Periodically, a pacing threshold test is conducted wherein the pacing pulse width and amplitude are reduced to determine a chronaxie value related to the pacing pulse width sufficient to capture the heart and rheobase value related to pulse amplitude sufficient to capture the heart. Such threshold or LOC test data are stored in memory, and the pacing pulse width and/or amplitude are automatically increased from the threshold levels to provide a "safety margin" to assure capture of the heart.

Similar lead related conditions can occur with cardioversion/defibrillation leads that can result in failure to cardiovert or defibrillate the heart at a programmed shock energy level. The failure of the delivered therapy can be dangerous to the patient and/or can necessitate applying further, higher energy, cardioversion/defibrillation shocks which increases discomfort of the patient and is wasteful of battery energy.

The issue of the integrity of pacing leads and ICD leads has been a serious concern over many years. Certain cardiac IPGs have been provided with the capability of storing EGM and event data prompted by the automatic determination of over sensing and undersensing of cardiac events, LOC events, out of range lead impedance measurements, etc., that can be telemetered to the external programmer when the physician interrogates the IPG or monitor and used by the clinician in evaluating lead function.

The lead impedance data and other parameter data, e.g., battery voltage, bipolar to unipolar lead switch events, error counts, LOC event data, etc., that is telemetered to the external programmer is typically compiled and displayed on a monitor and/or printed out for analysis by the clinician. The clinician may undertake real time IPG parameter reprogramming and testing and observe the monitored surface ECG to try to pinpoint a suspected lead related condition that is indicated by the data and/or patient and/or device symptoms.

Certain external programmers that address the analysis of such data and symptoms include those disclosed in the following U.S. Pat. No. 4,825,869 (Sasmor et al.); U.S. Pat. No. 5,660,183 (Chiang et al.); and U.S. Pat. No. 5,891,179 (Er et al.), all incorporated herein by reference. The '869 patent describes processing a variety of uplink telemetered atrial and ventricular EGM data, stored parameter and event data, and the surface ECG in rule-based algorithms for determining various IPG and lead malfunctions. The '183 patent also considers patient symptoms in an interactive probability based expert system that compares data and patient systems to stored diagnostic rules relating symptoms to etiologies to develop a prognosis. The '179 patent discloses a programmer that can be operated to provide a kind of time varying display of lead impedance values in relation to upper and lower impedance limits. The lead impedance values are derived from pacing pulse current and voltage values and are either measured and stored in the IPG memory at an earlier time or comprise current, real time values that are uplink telemetered to the programmer for processing and display.

The diagnosis of lead related data at a later time in such ways is useful, but it is believed preferable to provide a more immediate response to a lead related condition by the IPG or monitor. The retrieved data may be suspect if a lead related condition causes the stored or real time telemetered data to be inaccurate. The physician may mistakenly rely upon such data to maintain or change programmed pacing parameters and modes, particularly if a lead related condition is intermittent and is not diagnosed.

Many proposals have been advanced to determine if a lead related condition has occurred and to modify the IPG operation and/or to provide a warning that is perceptible by the patient or can be telemetered to the external programmer when the physician interrogates the IPG or monitor. In addition, it has been a goal to automatically detect a lead conductor related condition and respond by switching pacing pathways to use available lead conductors that appear to be functioning properly.

Prior art detection of lead related condition and various IPG responses to such detection are set forth in U.S. Pat. No. 4,140,131 (Dutcher et al.); U.S. Pat. No. 4,549,548 (Wittkampf et al.); U.S. Pat. No. 4,606,349 (Livingston et al.); U.S. Pat. No. 4,899,750 (Ekwall); U.S. Pat. No. 5,003,975 (Hafelfinger et al.); U.S. Pat. No. 5,137,021 (Wayne et al.); 5,156,149 (Iludrlik); U.S. Pat. No. 5,184,614 (Collins); 5,201,808 (Steinhaus et al.); U.S. Pat. No. 5,201,865 (Kuehn); U.S. Pat. No. 5,224,475 (Berg et al.); U.S. Pat. No. 5,344,430 (Berg et al.); U.S. Pat. No. 5,350,410 (Kieks et al.); U.S. Pat. No. 5,431,692 (Hansen et al.); U.S. Pat. No. 5,453,468 (Williams et al.); U.S. Pat. No. 5,507,786 (Morgan et al.); U.S. Pat. No. 5,534,018 (Walhstrand et al.); U.S. Pat. No. 5,549,646 (Katz et al.); U.S. Pat. No. 5,722,997 (Nedungadi et al.); U.S. Pat. No. 5,741,311 (McVenes et al.); U.S. Pat. No. 5,755,742 (Schuelke et al.); and U.S. Pat. No. 5,814,088 (Paul et al.). All of these patents are incorporated by reference.

Most of these patents disclose systems for periodically measuring lead impedance and comparing the impedance measurements with upper and lower impedance values or ranges and either storing the data for later retrieval, and/or changing a pacing or cardioversion/defibrillation path, and/ or adjusting the delivered pacing energy, and/or alerting the patient by generating sound or stimulation warning signals. Most of the above-incorporated patents depend on the generation of an impedance reading during a period of time when the pacemaker is not providing a stimulation pulse to the heart or, alternatively, sample and hold some portion or portions of a pacing signal, digitize some characteristic or characteristics inherent in that signal, and have that digitized signal processed by an on-board algorithm or circuit in order to produce an impedance value for the conductor under test. The impedance value is typically compared to upper and lower impedance thresholds, and employed as described above. In most cases, event data comprising the signal value and time and date are stored in memory whenever the impedance value exceeds or falls below the upper and lower impedance thresholds (i.e., the lead impedance is out of range). Certain of the above-incorporated patents, e.g. the '786 patent, also provide monitoring and storage of other parameters of IPG operation, e.g., battery voltage, for later retrieval and analysis by a clinician in an uplink telemetry session. Others of the above-incorporated patents disclose some processing of the lead impedance values within the IPG, and storage of the processed data for later retrieval and analysis by the clinician. The above-incorporated '975 patent discloses measuring unipolar and bipolar lead impedances, incrementing an error counter at least when the bipolar lead impedance value is out of range, and switching to a unipolar lead configuration, if one is available that exhibits a lead impedance value that is in the acceptable impedance range. The above-incorporated '750 patent discloses measuring output energy delivered during a pacing pulse, deriving a lead impedance value therefrom that is compared to a moving average impedance value, and incrementing a first error counter if a series, e.g., three, of such lead impedance values are out of range. In addition, characteristics of sensed heart signals are monitored, and the count of a second error counter is incremented if a series of the sensed heart signals exhibit an abnormality, e.g. an abnormal slew rate that could be due to a lead related condition. The counts are interrogated and displayed by an external programmer in an uplink telemetry session to alert the clinician of a possible lead related condition that should be investigated.

The above-incorporated '742 patent discloses an ICD lead impedance measurement system that measures impedance of all of the cardioversion/defibrillation leads and pacing leads using three leads at a time. A force lead and a measure lead are selected to drive current through a lead under test and to measure the voltage induced in the lead under test. Lead impedance values are derived and compared to upper and lower impedance thresholds. Out of range lead impedance value data causes an invalid flag to be set, may cause a patient warning to be emitted, and is stored as event data for later interrogation and uplink telemetry to the external programmer. The uplink-telemetered data is applied to sets of impedance rules for determining short circuit and open circuit lead related conditions. It is suggested that these rules and the testing process could be incorporated into the IPG to set a flag that identifies the lead defect and to emit a patient alert.

What the art has not yet shown is a self-testing system providing a lead status report that identifies particular lead related condition for each lead employed in the IMD. Optionally, such a monitor would cause a patient warning to be emitted and enable the IMD to alter its operating mode or to discontinue using a defective lead.

SUMMARY OF THE INVENTION

The present invention is particularly directed to a lead status monitor (LSM) incorporated into an IMD for processing lead related data in a system self test mode and providing a lead status report that identifies and declares conductor/connector issues, insulation issues, and electrode/tissue interface issues indicative of suspected lead related condition mechanisms for each lead employed in the IMD. The LSM operates employing a set of LSM rules that process measured lead impedance values and LOC values.

In accordance with one aspect of the present invention, the IMD comprises a cardiac pacing system, and particular LSM rules are defined that process periodically determined pacing pulse characteristics at LOC and periodically measured bipolar and unipolar lead impedance values. The lead impedance values are compared to upper and lower limits or trip points of a normal impedance range. When significant changes in lead impedance are detected, and the unipolar impedance values is compared to the bipolar lead impedance value of each lead. Counts of deviations in lead impedances satisfying each LSM rule are maintained. Certain of the lead related condition mechanisms are declared if a count of lead impedance deviations meets a programmed threshold number of such lead impedance deviations within a further programmed number of sequential impedance measurements.

Preferably, the pacing pulse strength or voltage at LOC (characterized as LOC_RHEOBASE herein) is periodically determined and compared to a reference LOC_RHEOBASE. Significant deviations in the last measured LOC_RHEOBASE from the reference LOC_RHEOBASE are employed in further LSM rules alone or in conjunction with certain of the lead impedance processing LSM rules to declare certain lead related condition mechanisms.

The lead status report declares suspected lead related condition mechanisms as suspected conductor/connector issues, insulation degradation issues and electrode/tissue interface issues. Preferably, the LOC_RHEOBASE ald/or lead impedance measurements and other event related data, including a short, digitized, EGM recording, are stored with the declarations for uplink telemetry and are reviewed by the clinician. Optionally, the system may include the capacity to warn the patient to seek assistance when a serious lead related condition mechanism is declared employing the LSM rules and the ability to switch a pacing path to avoid use of a lead conductor or an entire lead associated with a declared lead related condition mechanism.

When the lead status report is retrieved and displayed on an external programmer display via an uplink telemetry transmission, it provides the clinician with a clearer understanding of stored lead related data that may also accompany it. The clinician is able to determine the lead status much faster by testing the leads to verify whether the lead status report is correct. If it is correct and indicates a lead related condition mechanism, corrective action may be undertaken. If a declared conductor/connector issue, insulation issue and/or electrode/tissue interface issue is not considered to be correct upon further testing or analysis of uplink telemetered data, test parameters employed by LSM rules can be reprogrammed to ensure that the LSM rules are more likely to detect a true lead related condition mechanism of these types. And, the clinician can more quickly conduct verification tests to verify the accuracy of a lead status report that indicates that no lead related condition mechanism was detected since the last telemetry session.

It is desirable that the periodic telemetry sessions conducted by clinicians to assess patient condition and the integrity of the IMD and its functions be reduced in number and/or conducted by medical personnel other than physicians in order to reduce costs. The present invention is expected to increase confidence in the self-monitoring capacity of the IMD and to allow such changes to be made without compromising patient safety.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

In the following detailed description, references are made to illustrative cardiac IMD embodiments for carrying out the invention. It is understood that other IMD embodiments may be utilized without departing from the scope of the invention. The present invention can be implemented in any tissue stimulator where it is possible to determine lead impedance and if an applied electrical stimulation level is effective in causing a tissue reaction.

Figure 3:
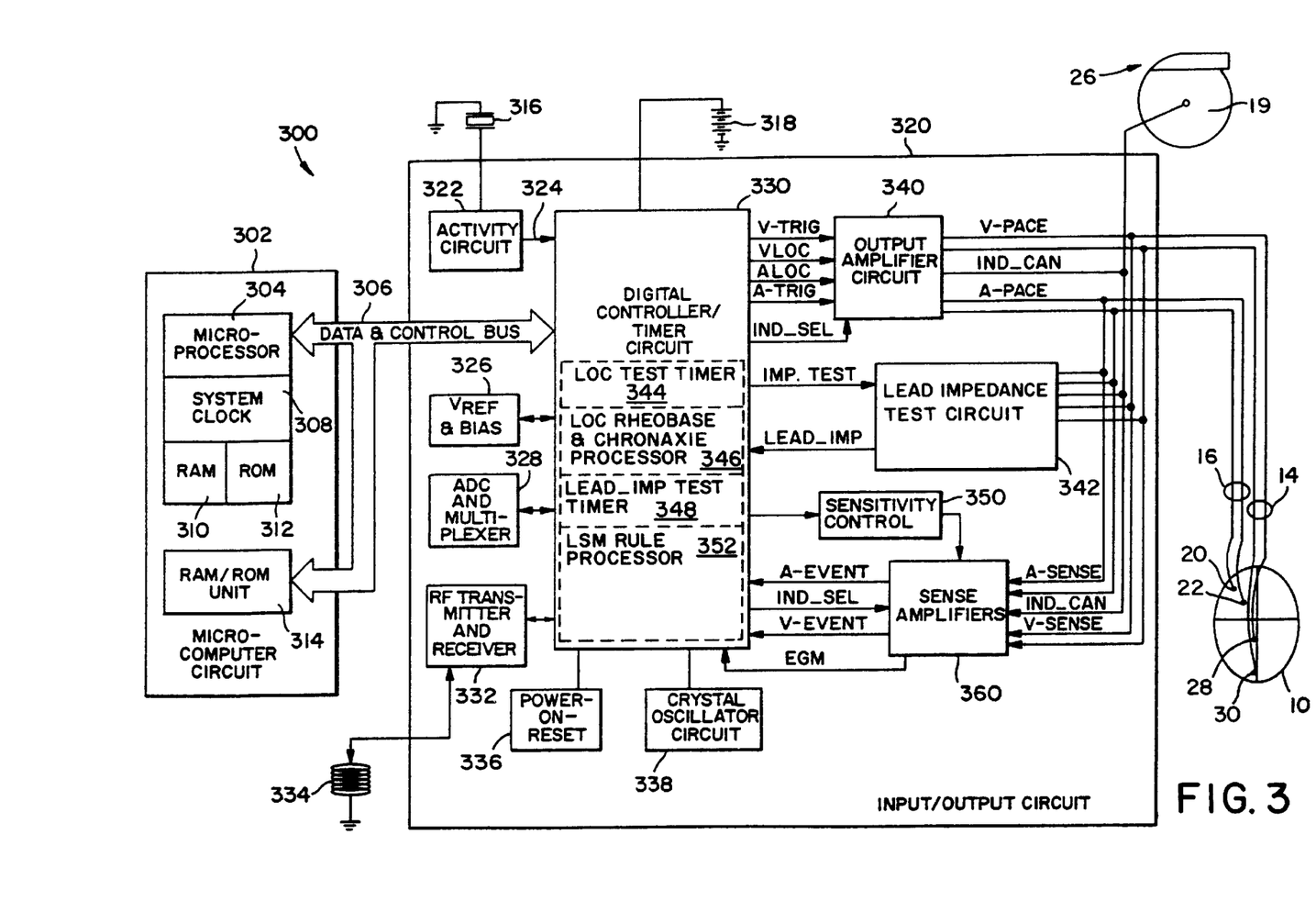
FIG. 3 is a block diagram of the dual chamber pacemaker illustrated in FIGS. 1 and 2, illustrating the functional components of the IPG in more detail.
Figure 4:
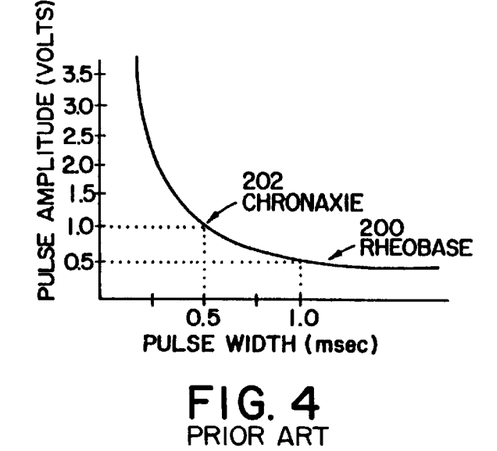
FIG. 4 is a typical strength-duration curve for cardiac stimulation signals.
Figure 5:
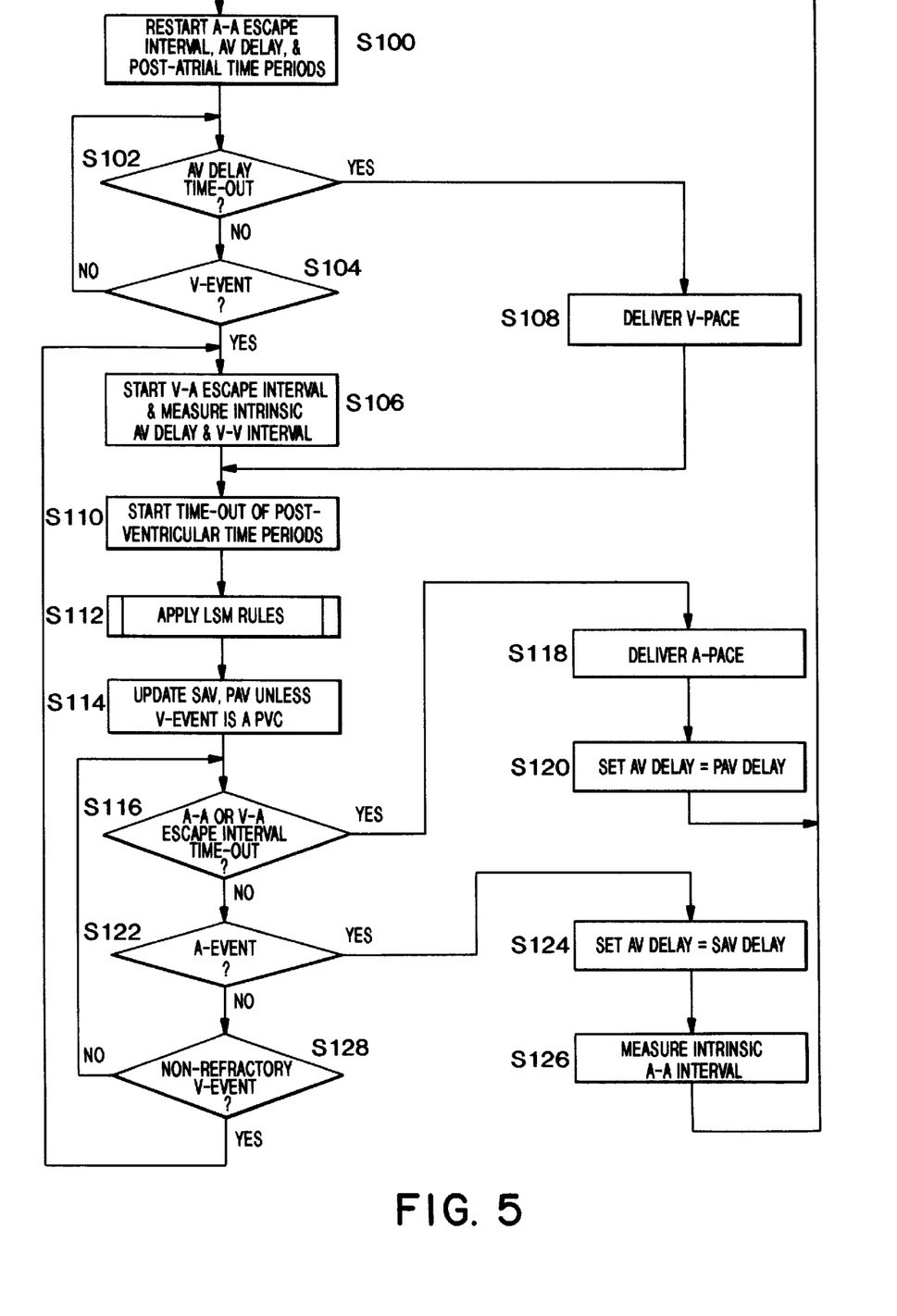
FIG. 5 is a flow chart of the overall operation of the pacemaker of FIGS. 1–3.

For example, the invention is disclosed in detail in FIGS. 1–4 in the context of an AV sequential pacing system operating in AV sequential pacing modes in accordance with FIG. 5 for restoring synchrony of the atria and ventricles. This embodiment of the invention is programmable to operate as an atrial or ventricular pacemaker. But it will be realized that the invention can also be practiced in a ventricular or atrial pacing system that can be dedicated to such use. It should also be appreciated that the pacing system of the present invention may be incorporated into an antitachyarrhythmia system including specific high rate pacing and cardioversion shock therapies for providing staged therapies to treat a diagnosed cardiac arrhythmia.

Figure 1:
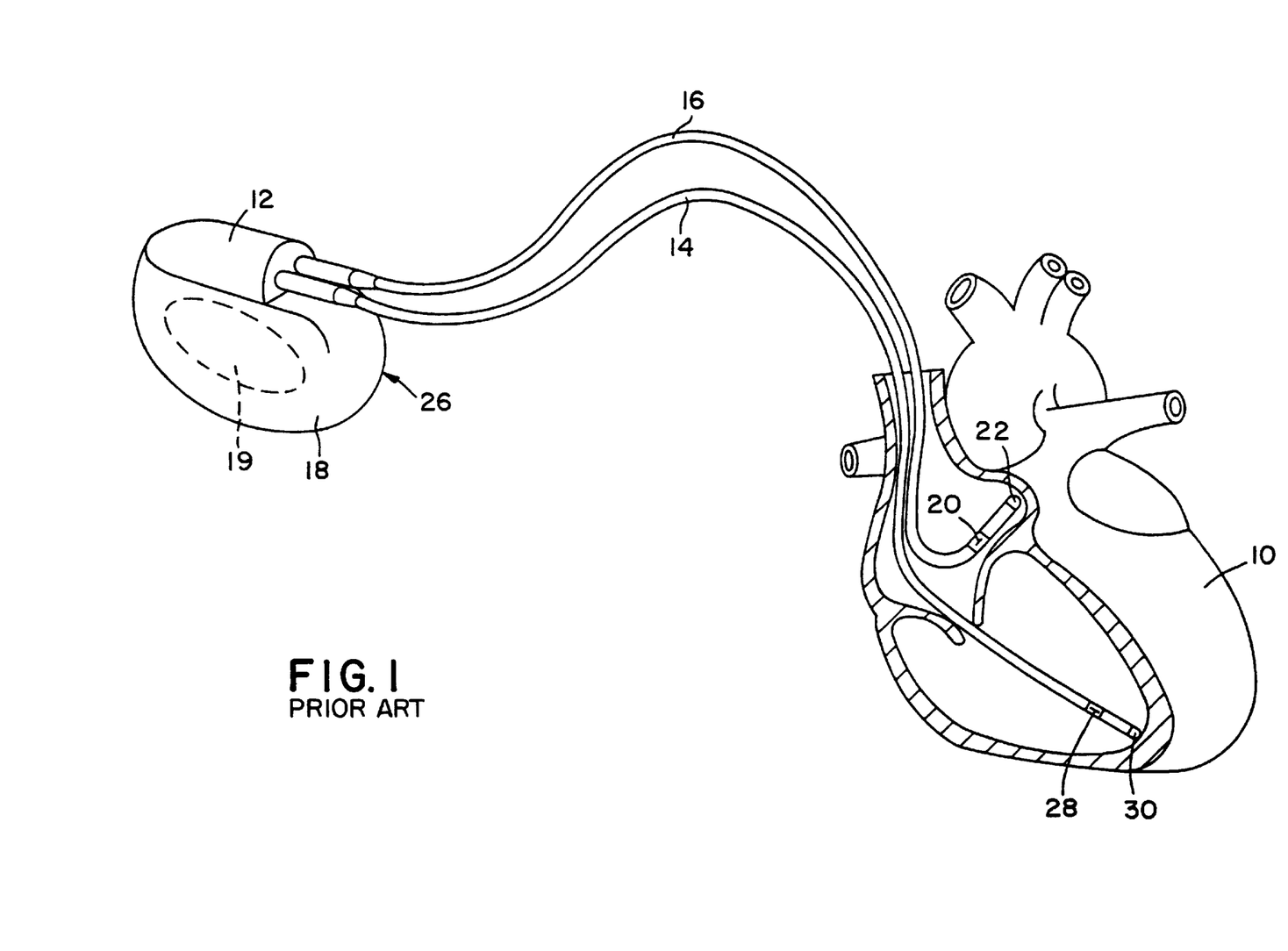
FIG. 1 is an illustration of a dual chamber pacemaker according to the present invention in conjunction with an associated set of cardiac pacing leads, illustrated as located in a cutaway view of a human heart.

FIG. 1 illustrates the external configuration of a dual chamber IPG 26, which is provided with a hermetically sealed can or housing 18, typically fabricated of biocompatible metal such as titanium. Mounted to the top of the housing 18 is a connector block assembly 12, which receives electrical connector elements located on the proximal ends of leads 14 and 16. The IPG housing 18 can be employed as a remote indifferent pace/sense electrode referred to herein as the IPG_CAN electrode 19. The combination of the leads 14 and 16 and the IPG 26 constitute an implantable pacemaker.

Lead 16 is an atrial bipolar pacing lead, carrying two electrodes 20 and 22 that are used both to sense atrial depolarizations (P-waves) and to deliver atrial pacing pulses. Atrial pacing pulses may be delivered between electrodes 20 and 22 in a bipolar pacing mode or between electrode 22 and IPG_CAN electrode 19 in a unipolar pacing mode. Sensing of P-waves may occur between electrode 20 and electrode 22 in a bipolar sensing mode or between either of electrode 20 and 22 and the IPG_CAN electrode 19 in a unipolar sensing mode.

Similarly, lead 14 represents a ventricular bipolar pacing lead, carrying two electrodes 28 and 30 that to are used to both sense ventricular depolarizations (R-waves) and to deliver ventricular pacing (V-PACE) pulses. Bipolar ventricular pacing may be accomplished between electrodes 30 and 28 or unipolar ventricular pacing may be accomplished between electrode 30 and the IPG_CAN electrode 19. Sensing of ventricular depolarizations or R-waves may be accomplished between electrodes 30 and 28 in a bipolar sensing mode or between either of electrodes 30 and 28 and the IPG_CAN electrode 19 in a unipolar sensing mode.

Such atrial and ventricular bipolar leads are typically formed having first and second lead conductors insulated from one another within a lead body insulating sheath. The distal tip or first pace/sense electrodes 22 and 30 and the ring or second pace/sense electrodes 20 and 28 and are located along the lead bodies of the atrial and ventricular leads 16 and 14, respectively. First and second lead connector elements (obscured within the connector block assembly 12) are located at the lead proximal end and are coupled to first and second connector elements in the connector block assembly 12. The first lead conductor extends between the first connector element and the distal or first pace/sense electrode, and is typically formed of an inner multi-filar wire coil having a coil lumen that accepts a stiffening stylet that is employed to assist in transvenous advancement of the lead distal end to the sites in the atria and ventricles depicted in FIG. 1, for example. The first conductor is located within the lumen of an inner insulating sheath, and the assembly is located within the lumen of a larger diameter, outer multi-filar wire coil that constitutes the second lead connector. The second lead conductor extends between the second connector element at the lead proximal end and the ring or second pace/sense electrode 20 and 28 in atrial and ventricular leads 16 and 14, respectively. An outer insulating sheath surrounds the second lead conductor. The atrial and ventricular pacing leads 16 and 14 can also be formed in other ways, e.g., by use of straight or coiled wire conductors that extend side-by-side molded within or inserted through separate channels of a common insulating sheath of the lead body. The elongated lead body is coupled to the proximal lead connector assembly distal electrode and any distal fixation mechanism in a manner that preserves the electrical isolation of the first and second lead conductors. In this way the first and second lead conductors are electrically insulated from one another and from the body as long as the insulation between them is not breached.

Atrial and ventricular pacing and sensing can be conducted using leads 16 and 14 in atrial and ventricular bipolar pacing pathways comprising a first IPG connector element coupled to the first lead connector element, the first lead conductor, the distal or first pace/sense electrode 22 or 30, the first electrode/tissue interface of the electrode surface with heart tissue and blood, the second electrode/tissue interface of the ring or second pace/sense electrode 20 or 28, respectively, the ring or second pace/sense electrode 20 or 28 itself, the second lead conductor, the second lead connector element coupled therewith, and a second IPG connector element coupled to the second lead connector element. Alternatively, atrial and ventricular pacing and sensing can be conducted using leads 16 and 14 in atrial and ventricular unipolar pacing pathways comprising the first IPG connector element coupled to the first lead connector element, the first lead conductor, the distal or first pace/sense electrode 22 or 30, the first electrode/tissue interface of the electrode surface with heart tissue and blood, the second electrode/tissue interface of the IPG_CAN electrode 19 with subcutaneous body tissue, the IPG_CAN electrode 19, itself and a direct electrical connection of the IPG_CAN electrode 19 to the IPG circuitry within housing 1.

The lead related condition mechanisms that can occur, when diagnosed by comparison to LSM rules as described herein, are characterized as conductor/connector open circuit issues, insulation degradation issues and electrode/tissue interface issues. The conductor/connector open circuit issues arise from a lead conductor fracture along its length or at the connections with the lead connector element or a pace/sense electrode or loosening of the connection between a lead connector element and its IPG connector element. The insulation degradation issues arise from a breach or perforation of the insulation of a lead conductor, resulting either in a short circuit with the other lead conductor in a bipolar lead or direct contact with body fluids or tissue, or both. The electrode/tissue interface issues arise from perforation or dislodgement of the pace/sense electrode from the original or optimal site of implantation in relation to the heart chamber or from exit block due to tissue reaction or growth at the site.

The determination of lead related condition mechanisms upon satisfaction of the LSM rules and the uplink telemetry of the determination and associated data in accordance with the present invention is preferably implemented in a pacing system operating in the DDD, DDI, DVI, DDDR, DVIR and DDIR pacing modes or in single chamber AAI and VVI pacing modes in a pacemaker or in an ICD. For ease of illustration, the specific embodiment of the IPG 26 disclosed as follows preferably operates in a DDD or DDDR pacing mode, wherein pacing pulses are delivered to both atrium and ventricle and wherein sensed atrial and ventricular depolarizations are both effective to inhibit delivery of the next scheduled pacing pulse in the chamber in which they are detected.

Figure 2:
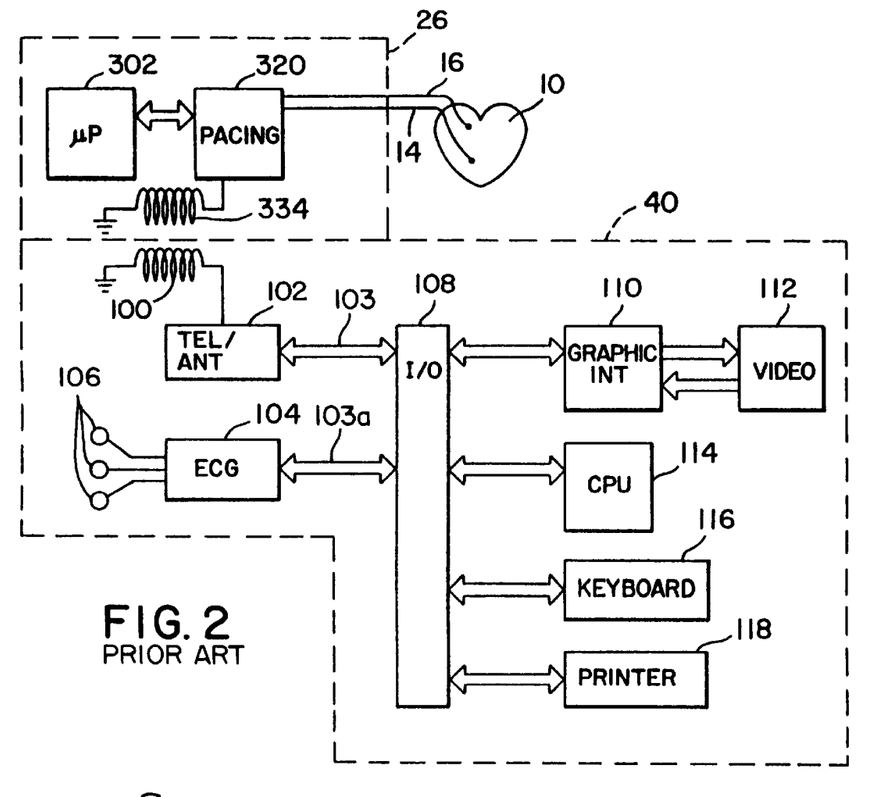
FIG. 2 is a functional block diagram of the dual chamber pacemaker illustrated in FIG. 1 in conjunction with an external programmer/monitoring unit, for use in performing the atrial and ventricular capture detection and auto threshold setting functions of the present invention.

FIG. 2 illustrates such an IPG 26 in block diagram form, coupled to a human heart 10 through the leads 14, 16, in conjunction with an external programmer 40 corresponding to those typically employed to program modern, multi-programmable implantable pacemakers for uplink telemetry of the lead related condition mechanism determinations upon satisfaction of the LSM rules and the associated data. The pacing circuitry 320, which includes circuitry performing all of the basic timing, stimulation and sensing functions of a DDD or DDDR cardiac pacemaker, and a microcomputer circuit 302, which controls the timing intervals provided by the pacing circuitry 320 within the housing of the IPG 26. Pacing circuitry 320 also includes a bidirectional telemetry circuit coupled to an antenna 334, allowing transmission of information from external programmer 40 into the IPG 26 to modify its parameters and allowing transmission of information from the IPG 26 to the external programmer 40, again generally corresponding to telemetry and programming systems presently existing in commercially marketed multi-programmable implantable pacemakers.

The programmer 40 also includes a telemetry antenna 100 coupled to a telemetry/antenna driver circuit 102 which serves to demodulate telemetry signals received from antenna 334 of the IPG 26, and to apply them in parallel or serial digital format to input/output (I/O) unit 108. The telemetry signals in turn may be applied to a video monitor 112, via graphic interface 110, and/or provided to central processing unit 114 and/or printer 118. Microprocessor 114 controls the operation of the programmer 40 and is responsive to physician entered commands via keyboard 116, for controlling programming signals sent to the IPG 26 and operation of the video display 112 and printer 118. Also illustrated in FIG. 2 is an ECG interface 104 coupled to three ECG electrodes 106 which are intended to be placed upon the patient's body. ECG interface 104 provides sensed electrograms to input/output device 108, where they in turn may be provided to the video display 112, the central processing unit 114 or the printer 118.

FIG. 3 depicts bipolar ventricular lead 14 and atrial lead 16 coupled with IPG circuit 300 having programmable modes and parameters and a telemetry transceiver of a DDDR type known in the pacing art. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, and the sense amplifiers circuit 360, as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Vref and Bias circuit 326 generates stable voltage reference and currents for the analog circuits within the pacing circuit 320, while analog to digital converter (ADC) and multiplexer circuit 328 digitizes analog signals and voltage to provide real time telemetry of cardiac EGM signals from sense amplifiers 360, for uplink transmission via RF transmitter and receiver circuit 332. Vref and Bias circuit 326, ADC and multiplexer circuit 328, power-on-reset circuit 336 and crystal oscillator circuit 338 may correspond to any of those employed in implantable cardiac pacemakers or ICDs.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 may take the form of a piezoelectric crystal transducer coupled to the interior surface of the IPG housing 18 as is well known in the art, and its output signal is processed and used as the RCP. A timed interrupt, e.g., every two seconds, may be provided in order to allow the microprocessor 304 to analyze the output of the activity circuit PAS 322 and update the basic V-A (or A—A or V—V) escape interval employed in the pacing cycle.

Data transmission to and from the external programmer is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art. Moreover the determination of lead related condition mechanisms upon satisfaction of the LSM rules and the uplink telemetry of the determination and associated data are also uplink transmitted during a telemetry session.

Microcomputer 302 contains a microprocessor 304 and associated system clock 308 and on-processor RAM and ROM circuits 310 and 312, respectively. In addition, microcomputer circuit 302 includes a separate RAM/ROM circuit 314 to provide additional memory capacity. Microprocessor 304 normally operates in a reduced power consumption mode and is interrupt driven. In one embodiment of the invention, microprocessor 304 is a custom microprocessor adapted to fetch and execute instructions stored in RAM/ROM circuit 314 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 304.

Microprocessor 304 is awakened in response to defined interrupt events, which may include A-TRIG and V-TRIG signals generated by timers in digital timer/controller circuit 330 and A-EVENT and V-EVENT signals generated by sense amplifiers circuit 360, among others. The specific values of the intervals and delays timed out by digital controller/timer circuit 330 are controlled by the microcomputer circuit 302 by means of data and control bus 306 from programmed-in parameter values and operating modes. Digital controller/timer circuit 330 includes a set of timing and associated logic circuits including discharge/recharge timers, an intrinsic interval timer for timing elapsed V-EVENT to V-EVENT (V—V) intervals or A-EVENT to A-EVENT (A—A) intervals, escape interval timers for timing A—A, V-A, and/or V—V pacing escape intervals, an AV delay interval timer for timing an AV delays from a preceding A-EVENT (SAV) or A-TRIG (PAV), a postventricular timer for timing post-ventricular time periods, and an upper rate interval (URI) timer. Microcomputer 302 controls the operational functions of digital controller/timer circuit 330, specifying which timing intervals are employed, and setting at least the programmed-in base timing intervals, via data and control bus 306. Digital controller/timer circuit 330 starts and times out these intervals and delays for controlling operation of the atrial and ventricular sense amplifiers in sense amplifiers circuit 360 and the atrial and ventricular pace pulse generators in output amplifiers circuit 340.

In addition, a real time clock is incorporated into the digital controller/timer circuit for a number of uses, including timing the time of day when tests, e.g., pacing and sensing threshold tests, are to be undertaken or to append a date and time stamp to event data stored in memory for later telemetry out to an external programmer in the manner depicted in FIG. 2.

The post-event timers time out the post-ventricular time periods following a V-EVENT or a V-TRIG and post-atrial time periods following an A-EVENT or A-TRIG.

The durations of the post-event time periods may also be selected as programmable parameters stored in the microcomputer 302. The post-ventricular time periods include the post-ventricular atrial refractory period (PVARP), a post-ventricular atrial blanking period (PVABP), a ventricular blanking period (VBP), and a ventricular refractory period (VRP). The post-atrial time periods include an atrial refractory period (ARP) during which an A-EVENT is ignored for the purpose of resetting the AV delay, and an atrial blanking period (ABP) during which atrial sensing is disabled. These post-atrial time periods time out concurrently with the time-out of the SAV or PAV delay started by an A-EVENT or an A-TRIG.

The microprocessor 304 also optionally calculates AV delays, postventricular time periods, and post-atrial time periods which vary with the sensor based escape interval established in response to the RCP(s) and/or with the intrinsic atrial rate. The variable AV delays are usually derived as a fraction of a maximum AV delay set for the pacing lower rate (i.e., the longest escape interval).

The output amplifier circuit 340 contains atrial and ventricular pace pulse generators corresponding to any of those presently employed in commercially marketed cardiac pacemakers providing atrial and ventricular pacing. In order to trigger generation of a V-PACE pulse, digital controller/timer circuit 330 generates a V-TRIG signal at the end of an AV delay provided by AV delay interval timer. Similarly, digital controller/timer circuit 330 generates an A-TRIG signal at the end of the V-A escape interval timed by an escape interval timer in order to trigger delivery of the A-PACE pulse. The output amplifier circuit 340 includes switching circuits for coupling selected pace/sense electrode pairs from among the atrial and ventricular leads 14 and 16 and the IND_CAN electrode 19 to the atrial and ventricular pulse generators so as to provide bipolar or unipolar atrial and/or ventricular pacing. The sense amplifiers circuit 360 contains sense amplifiers corresponding to any of those employed in current cardiac pacemakers and ICDs for atrial and ventricular pacing and sensing. It has been common in the prior art to use very high impedance P-wave and R-wave sense amplifiers to amplify the voltage difference signal that is generated across the sense electrode pairs by the passage of a cardiac depolarization. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 provides programmed sensitivity commands to the sensitivity control register 350 that control sensitivity settings of the atrial and ventricular sense amplifiers 360.

The sense amplifiers circuit 360 includes switching circuits for coupling selected atrial and ventricular lead conductors and the IND_CAN electrode 19 to the atrial and ventricular sense amplifiers for atrial and/or ventricular bipolar or unipolar sensing. The sense amplifiers circuit 360 also includes blanking circuits for uncoupling the selected pairs of the lead conductors and the IND_CAN electrode 19 from the inputs of the atrial and ventricular sense amplifiers during the ABP, PVABP and VBP before, during, and after delivery of a pacing pulse to any of the pace/sense electrode pairs to avoid saturation of the sense amplifiers.

The sense amplifiers circuit 360 also includes EGM sense amplifiers that provide analog atrial and ventricular EGM signals that are directed to the ADC and multiplexer 328 to be digitized when EGM storage is commanded or real time uplink telemetry sessions are enabled. In accordance with one aspect of he present invention, the storage of EGM event data in RAM is triggered when ISM rules are satisfied and any of the electrode/tissue or conductor/connector or insulation degradation issues are declared.

The atrial and ventricular output amplifiers in output amplifier circuit 340 can also be selectively operated in a threshold seeking operating mode that is conducted in response to the ALOC and VLOC test commands to determine the atrial and ventricular pace pulse width and amplitude at ALOC and VLOC in the manner described in the above-incorporated '012 patent. The ALOC and VLOC commands are preferably issued to commence the LOC test periodically, e.g., once every 24 hours, upon time-out of a LOC test timer 344. The derived atrial and ventricular LOC pulse width and amplitude data is applied to the lead status monitor (LSM) rule processor 352.

The above-incorporated '012 patent discloses a method of performing the stimulation threshold tests once a day, preferably in the night when the patient is presumed to be sleeping. FIG. 4 (corresponding to FIG. 5 of the '012 patent) shows a typical strength-duration (S-D) curve for electrical stimulation of myocardial tissue plotted as pulse amplitude in volts versus pulse width in milliseconds. The curve shows, inter alia, that the stimulation threshold increases with a decreasing pulse width, and thus decreases with an increasing pulse width, except that beyond the Rheobase 200, no further reductions in the amplitude threshold can be achieved. Thus, increasing the pulse width beyond about one millisecond (in the example shown) still requires a threshold of 0.5 volts. Also included on the curve for illustrative purposes is the Chronaxie 202, a measure of myocardial excitability, which is the point representing the lowest pulse width needed to have an amplitude threshold equal to twice the Rheobase threshold.

It is well known in the art to provide a safety margin between the actual delivered pacing pulse width and amplitude and the stimulation thresholds appearing in the strength-duration curve. The amount of the safety margin may change over time and must be balanced against the need to maximize battery life, as increased amplitude and pulse width will cause greater battery energy consumption. Physiological changes in the patient may alter the thresholds from the initial programmed value or values, and can lead to LOC due to inadequate pulse amplitude or pulse width.

The microcomputer 302 may be programmed with these algorithms to periodically, e.g. every night at a certain time when the patient would be sleeping, to automatically adjust the A-pace and V-pace output amplitude and pulse width to test for atrial and ventricular stimulation thresholds. The process followed derives and stores in RAM the Rheobase and Chronaxie stimulation threshold values resulting from the tests for use in the algorithms of the present invention and for later telemetry out. The values are also employed to automatically reset the normal pacing pulse width and amplitude, reflecting a safety margin, until the next test is conducted. In the process of testing for the thresholds, capture is restored on detection of ALOC and VLOC by applied backup A-pace or V-pace pulses at programmed pulse width and amplitude energy.

The lead impedance test circuit 342 conducts the unipolar and bipolar impedance testing during each delivery of each pacing pulse or preferably during the V-A escape interval time-out in the manner described in the above-incorporated '018 patent. In the latter method, a lead impedance test timer 348 times out a lead impedance test time period from a prior V-EVENT or V-TRIG and issues the IMP_TEST command to the lead impedance test circuit 342. The lead impedance test circuit 342 measures lead impedance of every available atrial and ventricular, unipolar and bipolar, pacing path in seriatim.

In accordance with the present invention, the stimulation threshold data derived in the LOC test, particularly the amplitude or rheobase values at ALOC and VLOC that are within established upper and lower amplitude limits, and the lead impedance data (LEAD_IMP data) output by the lead impedance test circuit are combined in a LSM self test mode that is conducted frequently each day by the LSM rule processor 352. The LEAD_IMP data and the LOC_RHEOBASE values are provided to the LSM rule processor 352 which applies the LSM rules to the measured data employing programmed or derived impedance trip points or reference values and ranges that are stored in RAM/ROM circuit 314. No data is stored If none of the LSM rules related to the implied lead related condition mechanisms of each conductor, the connector interface, insulation degradation, and the electrode/tissue interface are satisfied by the measured lead impedance values and the stored LOC stimulation pulse amplitude. But, a LSM report that identifies suspected lead related condition mechanisms as suspected conductor/connector issues, insulation degradation issues and electrode/tissue interface issues is generated by LSM rule processor 352 and stored in RAM if any of the LSM rules are satisfied. Other event related data can also be stored, including short duration EGM data from the identified lead.

In addition, a patient warning may be emitted as described in the above-incorporated '131 and '088 patents. Also, a bipolar lead configuration is preferably switched to the unipolar configuration as disclosed in the above-incorporated '975 patent, for example, if a measured bipolar lead impedance value satisfies a LSM rule described further below. The IND_SEL. signal is applied to the output amplifier circuit 340 and the sense amplifiers circuit 360 to substitute the IND_CAN pace/sense electrode 19 for one of the pace/sense electrodes 20 or 22, 28 or 30. Typically, the ring pace/sense electrode 20 or 28 is replaced by the IND_CAN electrode 19, and that configuration is again tested.

The illustrated IPG block diagram of FIG. 3 is merely exemplary, and corresponds to the general functional organization of most multi-programmable microprocessor controlled DDD(R) cardiac pacemakers or cardiac pacing systems embodied into ICDs presently commercially available. It is believed that the present invention is most readily practiced in the context of such a pacing system, and that the present invention can therefore readily be practiced using the basic hardware of existing microprocessor controlled dual chamber pacing systems, as presently available, with the invention implemented primarily by means of modifications to the software or firmware stored in the ROM 312 and with certain hardware logic and timing circuitry described above. However, the present invention may also be usefully practiced by means of a full custom integrated circuit, for example, a circuit taking the form of a state machine, in which a state counter serves to control an arithmetic logic unit to perform calculations according to a prescribed sequence of counter controlled steps. As such, the present invention should not be understood to be limited to a pacing system having an architecture as illustrated in FIG. 3, and a circuit architecture as illustrated in FIG. 3 is not believed to be a prerequisite to enjoying the benefits of the present invention.

FIG. 5 is a functional flow chart of the normal operation of the pacemaker illustrated in FIGS. 1, 2 and 3 in a DDD pacing mode. This flow chart is intended to reflect the overall function of the pacing system, rather than any particular software or firmware that must be employed. The flow chart focuses on the important functional aspects of the invention because the invention is not dependent upon any particular software or hardware configuration in order to be usefully practiced. For the sake of simplicity, functional steps corresponding to the provision of refractory and blanking periods and other operations that are not relevant to the practice of the invention have been omitted, to allow for easier understanding of the overall operational mode.

In the flow chart of FIG. 5, it is assumed that the basic timing of the pacing system is based around of the definition of an atrial escape interval (A—A escape interval or V-A escape interval) which may be fixed or may vary as a result of the output of the physiologic sensor, e.g. the activity sensor 316 of FIG. 3 in a manner described above. This A—A escape interval and the current sensed AV (SAV) delay or paced AV (PAV) delay are restarted at step S100 due to an A-EVENT sensed in step S122 or an A-PACE delivered in step S118, respectively, which terminate the escape interval being timed out in step S116. During the AV delay the operating system awaits either time-out of the current AV delay (PAV or SAV) at step S102 or provision of a V-EVENT at step S104 by the ventricular sense amplifier. A-VTRIG is generated to trigger delivery of a V-PACE at step S108 if the AV delay times out in step S102 without a V-EVENT sensed at step S104. The time-out of the AV delay is terminated if a V-EVENT is sensed at step S104, and a V-A escape interval is started in step S106 in substitution for the A—A escape interval started in step S100. The AV delay and the intrinsic V—V interval terminated by the V-EVENT in step S104 are measured for diagnostic and control purposes in step S106.

Figure 6:
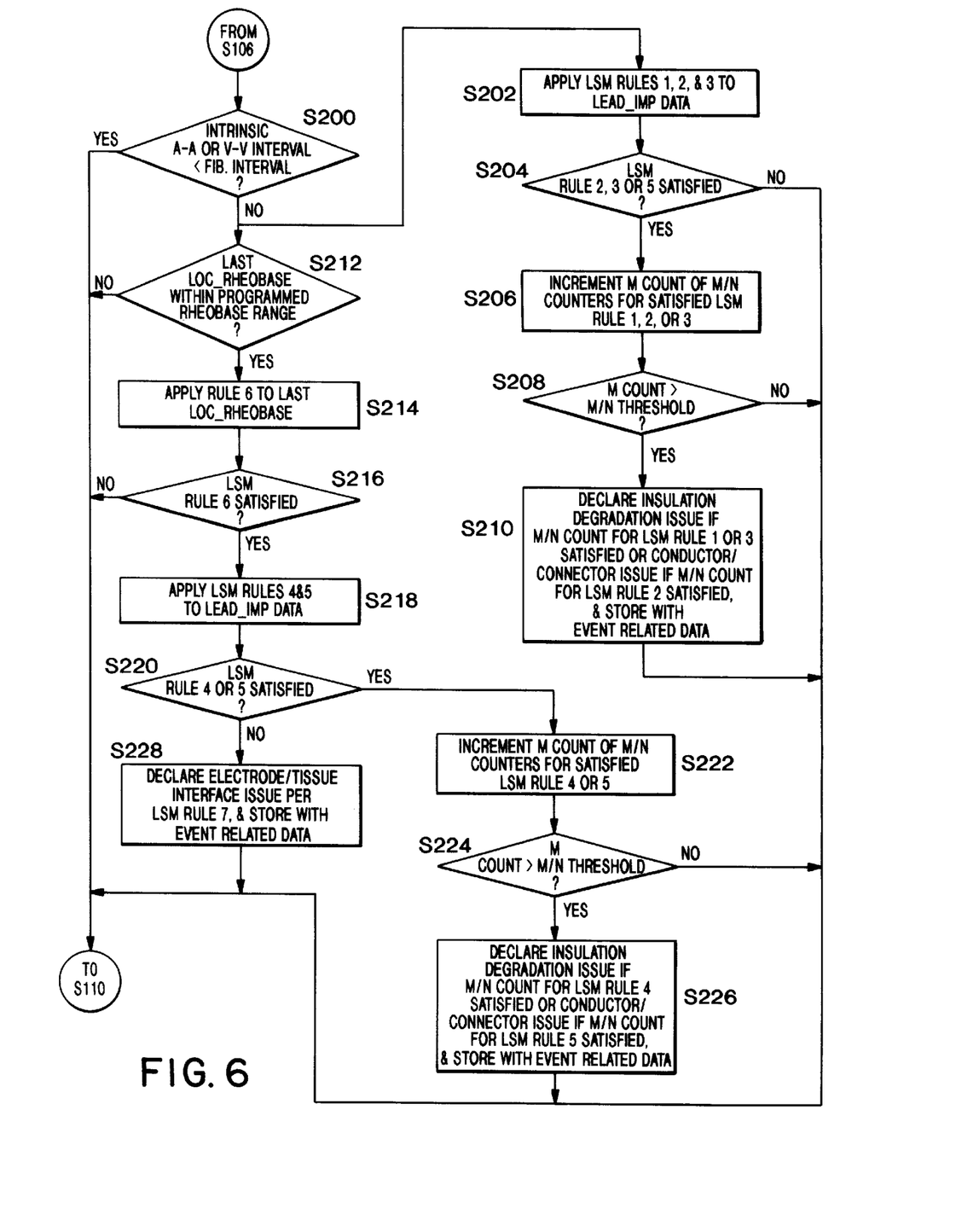
FIG. 6 is a simplified illustration of the LSM rules that are applied each time that the unipolar and bipolar lead impedance measurements are made in FIG. 5.

The post-ventricular time periods, e.g., the PVARP, PVABP, VRP, VBP, etc., are started in step S110 in response to either the time-out of the AV delay or the V-EVENT sensed in step S104. In step S112, the LSM rules described below are applied following the steps of FIG. 6. The LSM rules are defined below and rely upon the current unipolar and bipolar lead impedance measurements obtained during each pacing cycle, preferably during the V-A escape interval, and the most recently measured LOC_RHEOBASE value for the currently used atrial and ventricular pacing pathways. A recurring series of short V—V intervals is indicative of a high ventricular heart rate that may constitute ventricular tachycardia or fibrillation. As shown in FIG. 6, the LSM algorithm performed in step S112 is suspended until the high ventricular heart rate returns to a normal heart rate range.

At step S114, the SAV or PAV delays are updated as necessary based upon whether the preceding AV delay was terminated by a sensed V-EVENT or by its time-out. The A—A escape interval started in step S100 or the V-A escape interval started in step S106 continues to time out in step S116. The atrial and ventricular sense amplifiers are enabled to detect A-SENSE and V-SENSE depolarization waves after the PVABP and VBP, respectively, time out. In step S118, the A-TRIG signal is generated to trigger delivery of an A-PACE if the A—A or V-A escape interval does time out without a non-refractory A-EVENT or V-EVENT outputted by the atrial or ventricular sense amplifiers. When an A-PACE pulse is delivered in step S118, the next succeeding AV delay is defined to be equal to PAV at step S 120, and the A—A escape interval and the AV delay are restarted at step S100 to commence the next pacing cycle.

If an A-EVENT is provided by the atrial sense amplifier at step S122 prior to expiration of the A—A escape interval or V-A escape interval, then the subsequent AV delay is defined to be equal to SAV at step S124, and the A—A escape and AV delays are restarted at step S100. In addition, the intrinsic A—A interval terminated by the A-EVENT in step S122 is measured for diagnostic and control purposes in step S124. A recurring series of short A—A intervals is indicative of a high atrial heart rate that may constitute atrial tachycardia, flutter or fibrillation. Again, the LSM function of the present invention is suspended until the high atrial heart rate returns to a normal heart rate range.

The escape interval time-out in step S116 is terminated in the event that a non-refractory V-EVENT (characterized as a PVC) is sensed at step S128 prior to expiration of the A—A or V-A escape interval. The V-A escape interval is restarted in step S106, and steps S110–S 128 are repeated. However, in this case, the interval from the preceding V-PACE or V-EVENT and the PVC may be so short that the LSM rules are not applied as shown in the flow chart of FIG. 6. A V-event sensed at this point is also not effective to trigger an update of the SAV and PAV delays in step S114.

The LSM rules that are employed in the practice of the preferred embodiment of the invention are designed to provide an indication or declaration of suspected lead related condition or lead related condition mechanisms and supporting data in a lead status report stored in RAM. The declarations identify suspected conductor/connector issues, insulation degradation issues and electrode/tissue interface issues. The suspected lead related conditions are discerned by changes of the last, i.e., most recent, atrial and ventricular pacing path LOC—RHEOBASE values in relation to thresholds or average rheobase values or in conjunction with LEAD_IMP data derived from the same pacing pathways, or by detection of changes in bipolar and unipolar LEAD_ IMP data collected during each cardiac cycle. But an aberrantly large change of the last LOC_RHEOBASE value from the norm is discarded and not employed. Moreover, isolated changes in LEAD_IMP values that satisfy detection criteria are not sufficient to cause a declaration of a lead related condition. In accordance with the present invention, it is necessary that "M" LEAD_IMP values among the preceding "N" lead impedance measurements must satisfy a lead impedance LSM rule, before a declaration is issued. The numbers "N" and "M" may be programmable into RAM by the clinician employing the programmer of FIG. 2 and may differ for each LSM rule. Moreover, it will be appreciated that the number "M" can be programmed to "1" so that a single deviant LEAD_IMP value may trigger a declaration of a lead related condition mechanism and storage of associated data. However, the numeric range of programmable "M " numbers is typically greater than "1" but less than "N". The number "M" may be typically programmed from 1–32, for example, and the number "N" may be programmed from 16–32, for example.

FIG. 6 illustrates the application of the LSM rules in step S112 of FIG. 5 to each lead conductor in the lead set employed in the pacing system. The measured intrinsic A—A and/or V—V interval is compared to a threshold fibrillation interval in step S200, and the remaining steps of FIG. 6 are not followed to apply the LSM rules if the measured intrinsic A—A or V—V interval is shorter than a fibrillation or tachycardia interval. But, the LSM rules are applied in the remaining steps of FIG. 6 if there is no intrinsic A—A or V—V escape interval or they are longer than the fibrillation interval. In steps S202–S210, the LSM Rules 1–3 are processed using the LEAD_IMP data alone. In steps S212–S228, the LSM Rules 4–6 are processed using the LEAD_IMP data and the LOC_RHEOBASE data in combination. In step S228, the LOC_RHEOBASE data is used alone in processing LSM Rule 7. Steps S214–S228 and LSM Rules 4–7 are only practiced if the last LOC_ RHEOBASE value falls within the programmed rheobase range as determined in step S212. The processing of LSM Rules 1–3, 4–6 and 7 of the atrial and ventricular LOC_ RHEOBASE values and LEAD_IMP values is illustrated as taking place in parallel steps, but it will be understood that certain or all of the steps can be conducted in seriatim.

In step S202, the LEAD_IMP values for all of the tested pacing pathways are subjected to the LSM Rules 1–3 either simultaneously or in seriatim. The ISM processing of these LSM Rules 1–3 is completed if none are satisfied as determined in step S204. If at least one of the LSM Rules 1–3 is satisfied, then the "M" count of the M/N counter for that rule is incremented in step S206, and the M/N count is examined in step S208. The number "M" may be programmed to 8, for example, and the number "N" may be programmed to 15, for example. When "M" or 8 out of the preceding "N" or 15 LEAD_IMP values satisfy the criteria of a given LSM Rule, then a declaration will be issued in step S210, and the LEAD_IMP values will be stored with the declaration along with any other event related data, e.g., EGM data, that may be pertinent.

In step S202, LSM Rule 1 compares the measured LEAD_IMP value to a lower impedance range boundary or trigger point, e.g. 200 ohms, that may also be programmable, and increments the corresponding LSM Rule 1 "M" count in step S206 if the LEAD_IMP value falls below the lower impedance trigger point. When M/N LEAD_IMP values fall below the lower impedance trigger point, as determined in step S208, a declaration is stored in RAM that the lead under test may have an insulation issue, i.e., the outer insulation of the lead conductor or the inner insulation between lead conductors may be breached. The supporting LEAD_IMP data and other event related data may also be stored for retrieval and analysis along with the declaration.

In step S202, LSM Rule 2 compares the measured LEAD_IMP value for each lead to an upper impedance range boundary or trigger point, e.g. 4,000 ohms, that is also programmable, and increments the corresponding LSM Rule 2 "M" count in step S206 if the LEAD_IMP value exceeds the upper impedance trigger point. When M/N LEAD_IMP values exceed the upper impedance trigger point, as determined in step S208, a declaration is stored in RAM that the lead under test has a conductor/connector issue, i.e., there is an open circuit either by virtue of a broken conductor or connection therewith in the lead body or there is a loosened or separated connection between the lead connector element and the corresponding connector element of the IPG connector block assembly. Again, the supporting LEAD_IMP data and other event related data may also be stored for retrieval and analysis along with the declaration.

In step S202, LSM Rule 3 compares the measured unipolar LEAD_IMP value to the measured bipolar lead impedance value for each of the atrial and ventricular leads. Normally, chronic unipolar LEAD_IMP value is lower than the bipolar LEAD_IMP value due to the shorter lead conductor resistance in the latter case by a certain impedance difference value, e.g., 50 ohms, that is characteristic of the lead, and is also programmable by the clinician. If the bipolar LEAD_IMP falls below the bipolar/unipolar impedance trip point (the unipolar LEAD_IMP+50 ohms in this example), it indicates the possibility that the lead under test has an insulation issue, i.e., the inner insulation between lead conductors is likely breached allowing the lead conductors to make contact and to lower the observed bipolar lead impedance. When LSM Rule 3 is satisfied in step S204, the corresponding Rule 3 "M" count is incremented in step S206. A declaration is stored in RAM that the inner insulation between lead conductors is likely breached and the unipolar and bipolar LEAD_IMP data and other event related data are stored in RAM when the Rule 3 M/N count is achieved.

The LSM Rules 4 and 5 that process LEAD-IMP data are applied along with the LSM Rule 6 that processes atrial and ventricular LOC_RHEOBASE data in steps S214–S226. LSM Rule 6 has to be satisfied in step S216 before LSM Rules 4 and 5 are processed in steps S218–S226. LSM Rule 7 defines a default condition that is declared in step S228 when that LSM Rule 6 is satisfied but, neither LSM Rule 4 nor LSM Rule 5 is satisfied in step S220. A condition precedent to the processing of LSM Rules 4–7 must be satisfied in step S212: the last LOC_RHEOBASE must be found to be within a programmed upper and lower rheobase limit in step S212 before steps S214–S228 are undertaken. Any measured atrial and ventricular LOC_RHEOBASE values that exceed the upper voltage limit, which may be 2.5 volts, for example, or fall below the lower voltage limit, which may be 0.25 volts, for example, are presumed too unreliable to be employed and are excluded from consideration.

LSM Rule 6 compares the most recent 24-hour atrial and ventricular LOC_RHEOBASE values to reference atrial and ventricular LOC_RHEOBASE values, respectively, that are measured at implant and optionally again following subsidence of the typical tissue irritation that occurs where the distal tip pace/sense electrode contacts the endocardium. For example, the reference atrial and ventricular LOC_RHEOBASE values can be re-established at 90 days following implant and used thereafter. In this way, the reference atrial and ventricular LOC_RHEOBASE values that are measured at implant are employed in LSM Rules 6 and 7 during the first 90 days post-implant, and the reference atrial and ventricular LOC_RHEOBASE values that are measured at 90 days post-implant are used thereafter.

In operation, LSM Rule 6 determines if there is a substantial voltage change in the last measured LOC_RHEOBASE from the reference LOC_RHEOBASE value that is still within the upper and lower rheobase limits of step S212 but that exceeds a programmed voltage threshold change. If such a change occurs and is detected in step S216, it can signify an electrode/tissue issue, an insulation issue or a conductor/connector issue because the pacing threshold could increase in all three cases.

LSM Rules 4 and 5 compare the measured LEAD_IMP value to an average LEAD_IMP value that represents a running average of prior LEAD_IMP values, The average LEAD_IMP is determined, for example, from a number, e.g., 16, prior LEAD_IMP values by disregarding the four highest and the four lowest measured impedances and averaging the remaining 8 impedance values. LSM Rule 4 is satisfied when the current LEAD_IMP value increases above the average by a programmed factor, e.g., a factor of two or by 200%, which is suggestive of a conductor/connector open circuit related condition mode. LSM Rule 5 is satisfied when the current LEAD_IMP value decreases below the average by a programmed factor, e.g., a factor of one/half or 50%, which is suggestive of an insulation short circuit related condition mode.

In step S218, LSM Rules 4 and 5 are applied, and if either is satisfied in step S220, then the corresponding LSM Rule 4 or 5 "M" count is incremented in step. When the respective "M" count of the LSM Rule 4 M/N counter reaches the programmed "M" threshold in step S224, then a declaration is stored in RAM that the lead under test has an insulation issue, i.e., the outer insulation of the lead conductor or the inner insulation between lead conductors is likely breached, in step S226. When the respective "M" count of the LSM Rule 5 M/N counter reaches the programmed "M" threshold in step S224, then a declaration is stored in RAM that the lead under test has a conductor/connector issue in step S226. The LOC_RHEOBASE value and the LEAD_IMP data are also stored in step S226 with other relevant event data, e.g., EGM data.

The LSM Rule 7 criteria are satisfied in step S228 if LSM Rule 6 is satisfied in step S216, but neither LSM Rule 4 nor 5 is satisfied in step S220. An electrode/tissue interface issue is declared in step S228 and stored in RAM along with the measured LOC_RHEOBASE value and other relevant event data, e.g., EGM data.

The present invention can be implemented in conjunction with the derivation and storage of other lead related data, including open circuit pace (OCP) and short circuit pace (SCP) data and non-physiologic sense (NPS) data. One or more rolling count of number of times that a trip point of any of the LSM rules is exceeded in a predetermined period, e.g., the preceding 24 hours, can also be incorporated into the stored data for interrogation and uplink telemetry to an external programmer. For example, the number of times that a unipolar or bipolar lead impedance exceeds or falls below an impedance range upper or lower trip point can be accumulated on a 24 hour basis to provide additional data for use either clinically or use during a clinical evaluation of the performance of a particular lead.

It will be understood that certain of the above-described structures, functions and operations of the pacing systems of the preferred embodiments are not necessary to practice the present invention and are included in the description simply for completeness of an exemplary embodiment or embodiments. It will also be understood that there may be other structures, functions and operations ancillary to the typical operation of such pacing systems that are not disclosed and are not necessary to the practice of the present invention. In addition, it will be understood that specifically described structures, functions and operations set forth in the above-listed, commonly assigned and co-pending patent applications can be practiced in conjunction with the present invention, but they are not essential to its practice.

The above specification and the embodiments disclosed are intended to allow one of skill in the art to incorporate the present invention into a modern implantable cardiac pacing system of a cardiac pacemaker or ICD. However, it is of course understood that the particular implementation of the invention will vary depending upon the particular underlying circuitry types and software systems employed. In the following claims, means-plus-function clauses are intended to cover the structures described herein as performing the recited function and not only structural equivalents but also equivalent structures. The above disclosure should be considered exemplary, rather than limiting with regard to the claims that follow.

What is claimed is:

1. In an implantable medical device capable of delivering stimulation energy to the body for triggering a stimulus response comprising an implantable pulse generator coupled to one or more lead at a connector interface, each lead comprising a lead body extending between a lead connector element at a lead proximal end adapted to be coupled with the implantable pulse generator at a connector interface and a lead distal end, the lead body supporting an exposed electrode adapted to interface with tissue at an electrode/tissue interface and enclosing at least one electrical conductor that is insulated within the lead body and extends between the exposed electrode and the lead connector element, a lead status monitoring method for processing lead related data in a system self test mode and providing, for each lead, a lead status report that identifies suspected lead related condition mechanisms as suspected conductor/connector issues, insulation degradation issues and electrode/tissue interface issues, the method comprising the steps of:

establishing a set of lead status monitor rules related to the implied lead related condition mechanisms of each conductor itself, its connector interface, its insulation degradation, and its electrode/tissue interface;

periodically measuring the impedance of the lead and deriving a measured lead impedance;

periodically conducting a stimulation threshold test varying stimulation energy and monitoring the stimulus response to determine a loss of capture stimulation energy level at which the applied electrical stimulation energy fails to trigger a stimulus response;

subjecting the measured lead impedance and the loss of capture stimulation energy level to the set of lead status monitor rules; and generating the lead status report identifying any conductor/connector issues, insulation issues, and electrode/tissue interface issues that are implied when the measured lead impedance and loss of capture stimulation energy level satisfy one or more of the set of lead status monitor rules.

2. The method of claim 1, further comprising the step of storing the lead status report and event related data comprising one or more of the measured lead impedance, the loss of capture stimulation energy level and electrical signals of the body.

3. In a cardiac pacing system of the type comprising an implantable pulse generator for sensing cardiac activity and providing pacing pulses to at least one chamber of the heart through a pacing path, the pacing path comprising at least one pair of pace/sense electrodes, a like pair of electrode/tissue interfaces, and the body and heart tissue located therebetween, and at least one lead extending from the implantable pulse generator to the heart and locating at least one of the pace/sense electrodes of each pair at a site in relation to a heart chamber, each lead comprising an elongated lead body extending between a lead connector element at a lead proximal end adapted to be coupled with the implantable pulse generator at a connector interface and a lead distal end, the lead body supporting at least one exposed pace/sense electrode adapted to interface with tissue at an electrode/tissue interface and enclosing at least one electrical conductor within a lead body insulating sheath extending between the exposed electrode and the lead connector element, a lead status monitoring method for processing lead related data in a system self test mode and providing, for each lead pacing path, a lead status report that identifies suspected lead related condition mechanisms as suspected conductor/connector open circuit issues, insulation degradation issues and electrode/tissue interface issues, the method comprising the steps of:

establishing a set of lead status monitor rules related to implied lead related condition mechanisms of each conductor itself, its connector interface, its insulation degradation, and its electrode/tissue interface;

periodically, measuring the impedance of the lead or leads in the pacing path and deriving a measured lead impedance;

periodically conducting a pacing threshold test varying pacing pulse energy and monitoring the response of the heart chamber to determine a loss of capture pulse energy level at which the applied pacing pulse energy fails to capture the heart chamber;

subjecting the measured lead impedance and the loss of capture pulse energy level to the set of lead status monitor rules; and generating the lead status report for the pacing path identifying any conductor/connector open circuit issues, insulation degradation issues, and electrode/tissue interface issues that are implied when the measured lead impedance and loss of capture pulse energy level satisfy one or more of the set of lead status monitor rules.

4. The method of claim 3, wherein the step of conducting a pacing threshold test comprises, for each pacing path, the steps of:
   varying pacing pulse amplitude of a delivered pacing pulse delivered through the pacing path;
   monitoring the response of the heart to the delivered pacing pulse; and
   determining a measured rheobase value of the pulse amplitude of a delivered pacing pulse that results in loss of capture of the heart.

5. The method of claim 4, wherein the establishing step further comprises:
   establishing a reference rheobase;
   establishing a rheobase deviation from the reference rheobase; and
   defining a rheobase lead status monitor rule that when the measured rheobase value differs from the reference rheobase by the rheobase deviation, a suspected lead related condition mechanism at the electrode/tissue interface is declared.

6. The method of claim 4, wherein the establishing step further comprises:
   establishing a reference rheobase;
   establishing a rheobase deviation from the reference rheobase;
   establishing a reference lead impedance;
   defining an open circuit lead status monitor rule that when the measured lead impedance increases by a predetermined multiplier of the reference lead impedance during a predetermined number of successive lead impedance measurements and when the measured rheobase value differs from the reference rheobase by the rheobase deviation, a suspected lead related condition mechanism of the conductor or connector interface is declared.

7. The method of claim 4, wherein the establishing step further comprises:
   establishing a reference rheobase;
   establishing a rheobase deviation from the reference rheobase;
   establishing a reference lead impedance;
   defining an insulation degradation lead status monitor rule that when the measured lead impedance decreases to a predetermined fraction of the reference lead impedance during a predetermined number of successive lead impedance measurements and when the measured rheobase value differs from the reference rheobase by the rheobase deviation, a suspected lead related condition mechanism involving insulation degradation is declared.

8. The method of claim 3, wherein the establishing step further comprises:
   establishing a maximum reference impedance trip point;
   defining a maximum impedance lead status monitor rule that when the measured lead impedance value meets or exceeds the maximum reference impedance value during a predetermined number of successive lead impedance measurements, a suspected lead related condition mechanism of the conductor or connector interface is declared.

9. The method of claim 3, wherein the establishing step further comprises:
   establishing a minimum reference impedance trip point;
   defining a minimum impedance lead status monitor rule that when the measured lead impedance value equals or falls below the minimum reference impedance value during a predetermined number of successive lead impedance measurements, a suspected lead related condition mechanism of insulation degradation is declared.

10. The method of claim 3, wherein the implantable pulse generator comprises an implantable pulse generator housing capable of functioning as a remote indifferent pace/sense electrode in a unipolar lead configuration, and the lead comprises a bipolar lead having first and second lead conductors insulated from one another within said lead body insulating sheath, first and second pace/sense electrodes located along the lead body, and first and second lead connector elements located at the lead proximal end, the first lead conductor extending between the first connector element and the first pace/sense electrode, and the second lead conductor extending between the second connector element and the second pace/sense electrode, whereby pacing and sensing can be conducted in a bipolar pathway between the first and second lead connector elements or in a unipolar pathway between one of the first and second lead conductor elements and the remote indifferent pace/sense electrode, and wherein the establishing step further comprises:
   establishing a nominal lead impedance difference value between the bipolar lead impedance when lead impedance is measured in the bipolar configuration and the unipolar lead impedance is measured in the unipolar configuration; and
   defining a unipolar/bipolar impedance difference, lead status monitor rule that when the measured bipolar lead impedance value falls below the measured unipolar lead impedance by an amount that meets or exceeds the nominal lead impedance difference value during a predetermined number of successive lead impedance measurements, a suspected lead related condition mechanism of the insulation between the first and second conductors is declared.

11. The method of claim 3, further comprising the step of storing the lead status report and event related data comprising one or more of the measured lead impedance, the loss of capture stimulation energy level and the electrogram of the heart.

12. In an implantable medical device capable of delivering stimulation energy to the body for triggering a stimulus response, a lead status monitor for processing lead related data in a system self test mode and providing, for each lead, a lead status report that identifies suspected lead related condition mechanisms as suspected conductor/connector issues, insulation degradation issues and electrode/tissue interface issues, comprising:
   an implantable pulse generator adapted to be coupled to one or more lead at a connector interface,
   at least one lead comprising an elongated lead body extending between a lead connector element at a lead proximal end adapted to be coupled with the implantable pulse generator at the connector interface and a lead distal end, the lead body supporting an exposed electrode adapted to interface with tissue at an electrode/tissue interface and enclosing at least one electrical conductor within a lead body insulating sheath extending between the exposed electrode and the lead connector element, means for establishing a set of lead status monitor rules related to the implied lead related condition mechanisms of each conductor, the connector interface, insulation degradation, and the electrode/tissue interface;

means for periodically measuring the impedance of the lead and deriving a measured lead impedance;

means for periodically conducting a stimulation threshold test varying stimulation energy and monitoring the stimulus response to determine a loss of capture stimulation energy level at which the applied electrical stimulation energy fails to trigger a stimulus response;

means for subjecting the measured lead impedance and the loss of capture stimulation energy level to the set of lead status monitor rules; and means for generating the lead status report identifying any conductor/connector issues, insulation issues, and electrode/tissue interface issues that are implied when the measured lead impedance and loss of capture stimulation energy level satisfy one or more of the set of lead status monitor rules.

13. The system of claim 12, further comprising means for storing the lead status report and event related data comprising one or more of the measured lead impedance, the loss of capture stimulation energy level and electrical signals of the body.

14. In a cardiac pacing system, a lead status monitoring method for processing lead related data in a system self test mode and providing, for each lead pacing path, a lead status report that identifies suspected lead related condition mechanisms as suspected conductor/connector open circuit issues, insulation degradation issues and electrode/tissue interface issues, comprising:

an implantable pulse generator for sensing cardiac activity and providing pacing pulses to at least one chamber of the heart through a pacing path, the pacing path comprising at least one pair of pace/sense electrodes, a like pair of electrode/tissue interfaces, and the body and heart tissue located therebetween at least one lead extending from the implantable pulse generator to the heart and locating at least one of the pace/sense electrodes of each pair at a site in relation to a heart chamber, each lead comprising an elongated lead body extending between a lead connector element at a lead proximal end adapted to be coupled with the implantable pulse generator at a connector interface and a lead distal end, the lead body supporting at least one exposed pace/sense electrode adapted to interface with tissue at an electrode/tissue interface and enclosing at least one electrical conductor within a lead body insulating sheath extending between the exposed electrode and the lead connector element, means for establishing a set of lead status monitor rules related to implied lead related condition mechanisms of each conductor, the connector interface, insulation degradation, and the electrode/tissue interface;

means for periodically, measuring the impedance of the lead or leads in the pacing path and deriving a measured lead impedance;

means for periodically conducting a pacing threshold test varying pacing pulse energy and monitoring the response of the heart chamber to determine a loss of capture pulse energy level at which the applied pacing pulse energy fails to capture the heart chamber;

means for subjecting the measured lead impedance and the loss of capture pulse energy level to the set of lead status monitor rules; and means for generating the lead status report for the pacing path identifying any conductor/connector open circuit issues, insulation degradation issues, and electrode/tissue interface issues that are implied when the measured lead impedance and loss of capture pulse energy level satisfy one or more of the set of lead status monitor rules.

15. The cardiac pacing system of claim 14, wherein the means for conducting a pacing threshold test comprises, for each pacing path:

means for varying pacing pulse amplitude of a delivered pacing pulse delivered through the pacing path;

means for monitoring the response of the heart to the delivered pacing pulse; and means for determining a measured rheobase value of the pulse amplitude of a delivered pacing pulse that results in loss of capture of the heart.

16. The cardiac pacing system of claim 15, wherein the establishing means further comprises:

means for establishing a reference rheobase;

means for establishing a rheobase deviation from the reference rheobase; and means for defining a rheobase lead status monitor rule that when the measured rheobase value differs from the reference rheobase by the rheobase deviation, a suspected lead related condition mechanism at the electrode/tissue interface is declared.

17. The cardiac pacing system of claim 15, wherein the establishing means further comprises:

means for establishing a reference rheobase;

means for establishing a rheobase deviation from the reference rheobase;

means for establishing a reference lead impedance;

means for defining an open circuit lead status monitor rule that when the measured lead impedance increases by a predetermined multiplier of the reference lead impedance during a predetermined number of successive lead impedance measurements and when the measured rheobase value differs from the reference rheobase by the rheobase deviation, a suspected lead related condition mechanism of the conductor or connector interface is declared.

18. The cardiac pacing system of claim 15, wherein the establishing means further comprises:

means for establishing a reference rheobase;

means for establishing a rheobase deviation from the reference rheobase;

means for establishing a reference lead impedance;

means for defining an insulation degradation lead status monitor rule that when the measured lead impedance decreases to a predetermined fraction of the reference lead impedance during a predetermined number of successive lead impedance measurements and when the measured rheobase value differs from the reference rheobase by the rheobase deviation, a suspected lead related condition mechanism involving insulation degradation is declared.

19. The cardiac pacing system of claim 14, wherein the establishing means further comprises:

means for establishing a maximum reference impedance trip point;

means for defining a maximum impedance lead status monitor rule that when the measured lead impedance value meets or exceeds the maximum reference impedance value during a predetermined number of successive lead impedance measurements, a suspected lead related condition mechanism of the conductor or connector interface is declared.

20. The cardiac pacing system of claim 14, wherein the establishing means further comprises:
   means for establishing a minimum reference impedance trip point;
   means for defining a minimum impedance lead status monitor rule that when the measured lead impedance value equals or falls below the minimum reference impedance value during a predetermined number of successive lead impedance measurements, a suspected lead related condition mechanism of insulation degradation is declared.

21. The system of claim 14, further comprising means for storing the lead status report and event related data comprising one or more of the measured lead impedance, the loss of capture stimulation energy level and electrogram signals of the heart.

22. The cardiac pacing system of claim 14, wherein the implantable pulse generator comprises an implantable pulse generator housing capable of functioning as a remote indifferent pace/sense electrode in a unipolar lead configuration, and the lead comprises a bipolar lead having first and second lead conductors insulated from one another within said lead body insulating sheath, first and second pace/sense electrodes located along the lead body, and first and second lead connector elements located at the lead proximal end, the first lead conductor extending between the first connector element and the first pace/sense electrode, and the second lead conductor extending between the second connector element and the second pace/sense electrode, whereby pacing and sensing can be conducted in a bipolar pathway between the first and second lead connector elements or in a unipolar pathway between one of the first and second lead conductor elements and the remote indifferent pace/sense electrode, and wherein the establishing means further comprises:
   means for establishing a nominal lead impedance difference value between the bipolar lead impedance when lead impedance is measured in the bipolar configuration and the unipolar lead impedance is measured in the unipolar configuration; and
   means for defining a unipolar/bipolar impedance difference, lead status monitor rule that when the measured bipolar lead impedance value falls below the measured unipolar lead impedance by an amount that meets or exceeds the nominal lead impedance difference value during a predetermined number of successive lead impedance measurements, a suspected lead related condition mechanism of the insulation between the first and second conductors is declared.

* * * * *